(12) United States Patent
Sebti et al.

(10) Patent No.: US 9,453,049 B2
(45) Date of Patent: Sep. 27, 2016

(54) SUBSTRATE-MIMETIC AKT INHIBITOR

(71) Applicants: Said M. Sebti, Tampa, FL (US); Jin Q. Cheng, Tampa, FL (US); Andrew D. Hamilton, Oxford (GB); Katherine Kayser-Bricker, Brandford, CT (US)

(72) Inventors: Said M. Sebti, Tampa, FL (US); Jin Q. Cheng, Tampa, FL (US); Andrew D. Hamilton, Oxford (GB); Katherine Kayser-Bricker, Brandford, CT (US)

(73) Assignees: University of South Florida, Tampa, FL (US); Yale University, New Haven, CT (US)

( * ) Notice: Subject to any disclaimer, the term of this patent is extended or adjusted under 35 U.S.C. 154(b) by 0 days.

(21) Appl. No.: 14/472,966

(22) Filed: Aug. 29, 2014

(65) Prior Publication Data
US 2015/0004698 A1 Jan. 1, 2015

Related U.S. Application Data

(60) Division of application No. 12/480,329, filed on Jun. 8, 2009, now Pat. No. 8,822,524, which is a continuation of application No. PCT/US2007/086751, filed on Dec. 7, 2007.

(60) Provisional application No. 60/868,989, filed on Dec. 7, 2006.

(51) Int. Cl.

| | |
|---|---|
| A61K 31/404 | (2006.01) |
| A61K 31/132 | (2006.01) |
| C07D 209/04 | (2006.01) |
| C07C 255/50 | (2006.01) |
| C07C 255/51 | (2006.01) |
| C07K 7/06 | (2006.01) |
| C07K 5/02 | (2006.01) |
| C12N 9/12 | (2006.01) |
| C07C 255/60 | (2006.01) |
| C07C 279/12 | (2006.01) |
| C07D 209/14 | (2006.01) |
| C07K 5/06 | (2006.01) |
| C07K 5/08 | (2006.01) |
| C07K 5/10 | (2006.01) |
| A61K 38/00 | (2006.01) |

(52) U.S. Cl.
CPC .............. *C07K 7/06* (2013.01); *A61K 31/132* (2013.01); *A61K 31/404* (2013.01); *C07C 255/50* (2013.01); *C07C 255/51* (2013.01); *C07C 255/60* (2013.01); *C07C 279/12* (2013.01); *C07D 209/04* (2013.01); *C07D 209/14* (2013.01); *C07K 5/0207* (2013.01); *C07K 5/06* (2013.01); *C07K 5/08* (2013.01); *C07K 5/10* (2013.01); *C12N 9/12* (2013.01); *C12N 9/1205* (2013.01); *A61K 38/00* (2013.01); *C07C 2101/16* (2013.01); *C12Y 207/11001* (2013.01)

(58) Field of Classification Search
None
See application file for complete search history.

(56) References Cited

U.S. PATENT DOCUMENTS 6,156,766 A * 12/2000 Arita .................... C07D 213/75
514/241

* cited by examiner

*Primary Examiner* — Samantha Shterengarts
(74) *Attorney, Agent, or Firm* — Robert J. Varkonyi; Smith & Hopen, P.A.

(57) ABSTRACT

Disclosed herein is a species of peptide and non-peptide inhibitors of Akt, an oncogenic protein. Beginning with a residue of Akt target substrate GSK-3, the functional domains of the GSK-3 residue were characterized. Functionally homologous non-peptide groups were substituted for the amino acids of the GSK-3 creating a hybrid peptide-non-peptide and non-peptide compounds capable of binding to Akt. The non-peptide compounds show increased stability and rigidity compared to peptide counterparts and are less susceptible to degradation. The bound non-peptide compounds exhibit an inhibitory effect on Akt, similar to peptide-based Akt inhibitors.

13 Claims, 11 Drawing Sheets

| Compound | | IC₅₀ (μM) |
|---|---|---|
| 1 | Ac-G R P R T T W F -OH | >500 |
| 2 | Ac-G R P R T T F F -OH | >500 |
| 3 | Ac-G R P R T T H F -OH | >500 |
| 4 | Ac-G R P R T T V F -OH | 445 |
| 5 | Ac-G R P R T T A F -OH | 409 |
| 6 | Ac-G R P R T T C F -OH | 241 |
| 7 | Ac-G R P R T T N F -OH | 229 |
| 8 | Ac-G R P R T T V F -NH-(cyclohexyl) | 239 |
| 9 | Ac-G R P R A A V F -NH-(cyclohexyl) | 438 |
| 10 | Ac-G R P R Abz V F -NH-(cyclohexyl) | 28 |
| 11 | Ac-G R P R Abz V F -NH-(naphthyl) | 36 |
| 12 | Ac-G R P R Abz V F -NH-(alkyl) | 52 |
| 13 | Ac-G R P R Abz V F -NH-(naphthyl) | 62 |
| 14 | Ac-G R P R Abz V F -NH-(biphenyl) | 94 |
| 15 | Ac-G R P R Abz V F -NH-(alkylphenyl) | 96 |
| 16 | Ac-G R P R Abz V F -NH-(OCONH) | 322 |
| 17 | Ac-G R P R Abz V F -NH-(piperidine) | >500 |
| 18 | Ac-G A P R Abz V F -NH-(cyclohexyl) | 79 |
| 19 | Ac-G R P A Abz V F -NH-(cyclohexyl) | 41 |
| 20 | Ac-G A P A Abz V F -NH-(cyclohexyl) | >500 |
| 21 | Ac-R Abz V F -NH-(naphthyl) | 51 |
| 22 | Ac-R Abz V F -NH-(naphthyl) | 89 |
| 23 | Ac-R Abz V F -NH-(alkylphenyl) | 104 |
| 24 | Ac-R Abz V F -NH-(cyclohexyl) | 119 |
| 25 | Ac-R Abz V F -NH-(alkyl) | 163 |
| 26 | H₂N-(linker)-Abz V F -NH-(cyclohexyl) | 193 |

Figure 3.

| Compound | N-Terminus | | | | $R_1$ | $R_2$ | C-Terminus | | | $IC_{50}^a$ (μM) |
|---|---|---|---|---|---|---|---|---|---|---|
| 37 | Ac- G | R | P | R | -H | -H | V | F | -Bn | 28 |
| 38 | Ac- G | R | P | R | -CH₃ | -H | V | F | -Bn | 50 |
| 39 | Ac- G | R | P | R | -Ph | -H | V | F | -Bn | >500 |
| 40 | Ac- G | R | P | R | -H | -Ph | V | F | -Bn | 16 |
| 41 | Ac- G | R | P | R | -H | -1-Nap | V | F | -Bn | 78 |
| 42 | | | Ac- | R | -Ph | -H | V | F | -Bn | 288 |
| 43 | | | Ac- | R | -H | -Ph | V | F | -Bn | 173 |
| 44 | | | Ac- | R | -H | -H | V | F | -Bn | 119 |

| Compound | R₁ | R₂ | IC₅₀ᵃ (μM) |
|---|---|---|---|
| 56aa | -H | phenyl | 96 |
| 56ba | phenyl | phenyl | 84 |
| 56bb | phenyl | 4-methylphenyl | 215 |
| 56bc | phenyl | 2-methylphenyl | 152 |
| 56bd | phenyl | 4-phenylphenyl | 84 |
| 56be | phenyl | 4-fluorophenyl | 55 |
| 56bf | phenyl | naphthyl | 43 |
| 56bg | phenyl | 4-isopropylphenyl | 28 |
| 56bh | phenyl | 4-cyclohexylphenyl | 23 |
| 56bi | phenyl | 4-cyanophenyl | 19 |
| 56cg | naphthyl | 4-isopropylphenyl | 38 |
| 56ci | naphthyl | 4-cyanophenyl | 17 |
| 57aa | 4-NHCOCH₃-phenyl | phenyl | 253 |
| 57ba | 4-CO₂CH₃-phenyl | phenyl | 158 |
| 57ca | biphenyl | phenyl | 83 |
| 57da | 4-CN-phenyl | phenyl | 78 |
| 57ea | 4-isopropylphenyl | phenyl | 52 |
| 57fa | naphthyl | phenyl | 44 |

SUBSTRATE-MIMETIC AKT INHIBITOR

CROSS REFERENCE TO RELATED APPLICATIONS

This application is a divisional application of Ser. No. 12/480,329, entitled "Substrate-Mimetic AKT Inhibitor", filed on Jun. 8, 2009, which claims priority to prior-filed International Application, Serial Number PCT/US2007/086751 filed Dec. 7, 2007, which claims priority to U.S. provisional patent application No. 60/868,989 filed Dec. 7, 2006, the contents of which are hereby incorporated by reference into this disclosure.

GOVERNMENT INTEREST

This invention was made with Government support under Grant No. 1R01 CA107078-01, awarded by the National Institutes of Health. The Government may therefore have certain rights in the invention.

FIELD OF INVENTION

This invention relates to oncogenic prevention and treatment. Specifically, the invention relates to using substrate inhibitors to block the effects of Akt, also known as protein kinase B (PKB).

BACKGROUND OF THE INVENTION

Akt/protein kinase B (PKB) has been shown to be a widely expressed Ser/Thr protein kinase whose persistent activation leads to human oncogenesis. Its role in cancer and chemoresistance is accomplished by the concomitant promotion of cell growth, migration, and angiogenesis as well as the suppression of the apoptotic pathway. There has been significant interest in Akt for its structural and functional properties as well as its implications in the area of cancer therapy.

The Akt family consists of three members, Akt1 (PKBα), Akt2 (PKBβ), and Akt3 (PKBγ); that are structurally very similar (>85% sequence homology). Each isoform consists of an N-terminal pleckstrin homology (PH) domain, a central catalytic domain, and a C-terminal regulatory tail.

Stimuli activating Akt includes molecules that regulate tyrosine kinase activity and G-protein-linked receptors, cAMP/PKA agonists, and phosphatase inhibitors. Direct activation of Akt is mediated by agonist-induced stimulation of phosphoinositide-3 kinase (PI3K), which generates phosphatidylinositol-3,4,5-triphosphate ($PIP_3$), a lipid second messenger which binds to the PH domain of Akt and translocates it to the intracellular side of the plasma membrane. Anchored to the plasma membrane, Akt then undergoes dual phosphorylation by membrane associated protein kinases PDK1 and PDK2 on a pair of serine and threonine residues respectively (Thr308 in the activation loop and Ser473 in the C-terminal hydrophobic motif). This dual phosphorylation induces a conformational change in the enzyme to its activated form, which incorporates and ATP binding site as well as a substrate binding site.

Akt directly phosphorylates substrates that are involved in the regulation of numerous cellular functions such as cellular proliferation, transcription, migration, apoptosis, cellular differentiation, and metabolism. The disregulation of Akt kinase activity has been detected in a number of human malignancies including ovarian, breast, thyroid, and colon cancers. Amplification or overexpression of Akt results in the up-regulation of cell growth and the down-regulation of apoptosis. The cellular levels of $PIP_3$ regulate the activity of PDK-1, which is responsible for Akt activation. The levels of these phosphoinositides are dependent on the activity of PI3K and phosphatases PTEN and SHIP. Tumor suppressor PTEN negatively regulates the activity of Akt by converting $PIP_3$ back to $PIP_2$.

Inhibition of Akt activity has been shown to suppress cell growth and induce apoptosis in tumor cell lines derived from various organs possessing constitutively activated Akt. Akt activation causes the phosphorylation and inactivation of key cell maintenance proteins, like glycogen synthase kinase-3 (GSK-3). Normally active, Akt phosphorylates $Ser^{21}$ on GSK-3α or $Ser^9$ on GSK-3β, thereby inactivating GSK-3. GSK-3 is a cytoplasmic serine-theronine kinase existing in two isoforms, GSK-3α (51 kDa) and GSK-3β (47 kDa). The isoforms retain 98% homology in kinase domains, but only 36% homology in the last 76 amino acid residues in the C-terminus. GSK-3 is responsible for regulating cellular metabolism and is involved in insulin, Wnt, developmental and sonic hedgehog signaling pathways.

The majority of small molecule kinase inhibitors target the ATP binding pocket and there have been few reports targeting the substrate binding site. ATP mimetics have met with much success, however selective binding within this pocket remains challenging as these inhibitors compete with the many ATP utilizing enzyme possessing similar contact regions as well as with high cellular concentrations of ATP. Substrate-mimetics offer a promising method for the design of selective in vivo inhibitors of Akt as they can exploit sequence specificity. The substrate binding region has evolved to recognize specific substrate sequences and therefore offers a larger number of potential interactions for a properly designed inhibitor than the corresponding ATP pocket. The inherent design challenges present in substrate-mimetics are the large binding pocket and extended binding conformation of many natural substrates. We recently described the development of substrate-mimetic inhibitors of Akt based on the consensus sequence and the structure of an enzyme bound substrate. The preliminary studies demonstrate that limited structural modification of the initial peptidic substrate can overcome these challenges and provide peptidomimetic inhibitors with increasing lipophilicity, rigidity, and potency as well as decreasing the size and peptidic nature of the inhibitors.

SUMMARY OF INVENTION

Much effort has been applied to the development of Akt inhibitors that target the ATP binding domain of the protein, but these have the potential to affect other kinases or the many ATP utilizing enzymes. Recently there has also been an emergence of allosteric inhibitors which has met with some success. However, as a general point of strategy, targeting inhibitors to the peptide substrate binding site has the potential for the greater selectivity since it has evolved to respond to a highly specific sequence of amino acids. The substrate-binding site offers a large number of potential interactions to a small molecule derived through mimicry of the key peptide sequence providing a good opportunity for development of an Akt selective inhibitor. The X-ray crystal structure of an activated Akt ternary complex with a cellular substrate glycogen synthase kinase 3 (GSK3), and an ATP analogue identifies the GSK3 peptide (GRPRTTSF) to be bound in an essentially extended conformation, with discrete sections of β-strand on either side of the modifiable serine residue (FIG. 1). Extensive hydrogen bonding interactions are observed between acidic pockets of the protein and N-terminal basic residues of GSK3, while C-terminal interactions are essentially hydrophobic. The consensus substrate for processing has been shown to be Arg-$X_{aa}$-Arg-$Y_{aa}$-$Y_{aa}$-S/T-Hyd, where $X_{aa}$ may be any amino acid, $Y_{aa}$ any small amino acid other than glycine, and Hyd represents a large hydrophobic amino acid.

BRIEF DESCRIPTION OF THE DRAWINGS

For a fuller understanding of the invention, reference should be made to the following detailed description, taken in connection with the accompanying drawings, in which:

FIG. 3 is a table of initial peptide inhibitors of Akt, with the effective dosage concentrations.

FIG. 14 is a table showing the optimization of C-terminal and central substituents for non-peptide inhibitors. [a] Reported values are an average of three independent-binding curves utilizing an IMAP® Akt Assay Kit (Molecular Devices). Reactions were conducted in wells with 20.0 µL of 10 mM Tris-HCl (pH 7.2), 10 mM $MgCl_2$, 0.1% BSA, 0.05% $NaN_3$, 1 mM DTT, 100 nM 5FAM-GRPRTSSFAEG-COOH, 5 µM ATP, Akt1, and inhibitor. Reaction mixtures were incubated for 1 h at room temperature and then quenched with 60 µL of the IMAP-binding solution. The reactions were equilibrated for 1 h at room temperature then data points were collected and analyzed. (Inhibitors 56aa-ci synthesized via the reaction scheme depicted in FIG. 13, Inhibitors 57aa-fa synthesized via the reaction scheme depicted in FIG. 15.)

FIG. 17 is an illustration of the crystalline structure of the enzyme-bound compound number 71a, the solvent-accessible surface area of activated Akt, and ATP analogue. The Akt surface is shown in a gradient scale with FIG. 18 is a diagram of the chemical structure of compound number 71a.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The invention includes a process for on.

The first non-peptidic, substrate-mimetic inhibitor of Akt was developed through systematic rigidification and replacement of the remaining amino acid residues.

Figure 1:
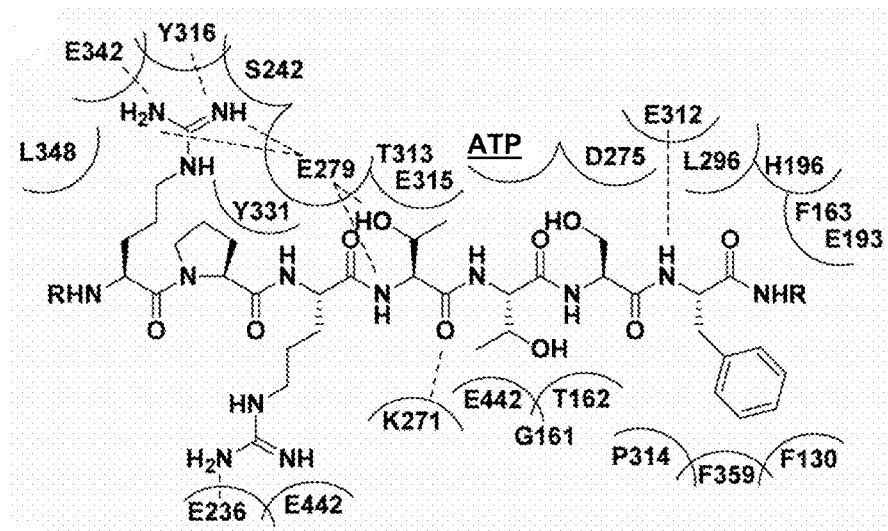
FIG. 1 is a diagram of the interaction between activated Akt, a GSK-3 residue, and ATP analogue, based on X-ray crystallography.
Figure 2:
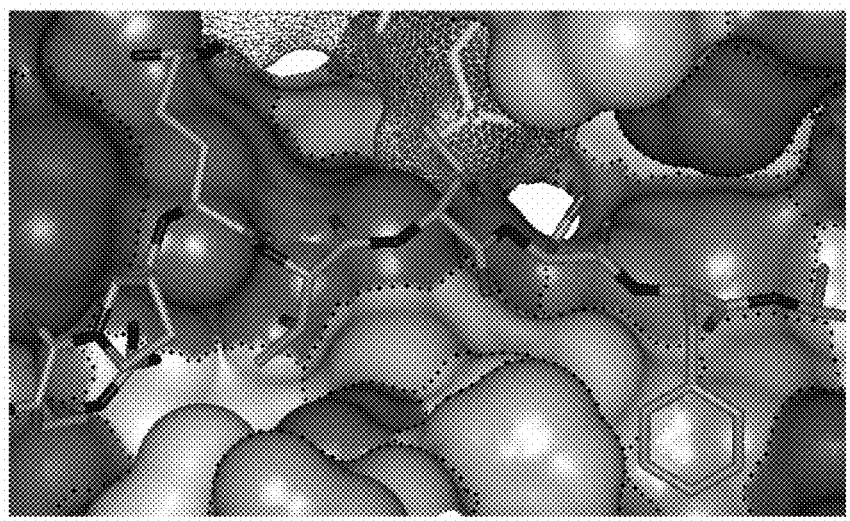
FIG. 2 is an illustration of the crystalline structure of the enzyme-bound GSK-3 residue, the solvent-accessible surface area of activated Akt, and ATP analogue. The Akt surface is shown in a gradient scale with a dashed line delineating the boundaries of the hydrophobic/hydrophilic regions.

The substrate-mimetic inhibitor design was based on the truncated GSK3β substrate sequence, GRPRTTSF, utilizing a recently published X-ray crystal structure of activated Akt ternary complex with GSK3β and an ATP analogue. The rational design approach was focused on reducing the entropy cost of the extended binding conformation, accessing a large unoccupied hydrophobic pocket adjacent to the C-terminus, and eliminating nonessential amino acid residues. This approach identified inhibitor 1 with in vitro Akt inhibition of IC$_{50}$=14 μM, seen in FIGS. 1 and 2.

Peptidomimetic inhibitors were generated directly from the minimal substrate sequence by systematic replacement of the non-critical amino acids and tested for in vitro inhibition of Akt using a fluorescence polarization assay system, shown in FIG. 3. Evaluating of the contribution of amino acids residues on GSK3, through scanning serine substitutions with several other L-amino acids, produced weakly binding peptidic inhibitors 1-7, see FIG. 3. Replacement of the reactive serine with a valine residue (a non-nucleophilic surrogate) in peptide 4 provided a starting point in the inhibitor design.

A benzyl (Bn), a small hydrophobic group, was included at the C-terminus to complement the unoccupied hydrophobic pocket afforded inhibitor 8 a 2-fold increase in potency (IC$_{50}$ of 239 μM). The internal -TT- residues, which make few interactions with the protein surface, were then replaced with -AA-, resulting in a two-fold decrease in activity, however, substitution with a conformationally restricted scaffold, p-amino benzoic acid (Abz), afforded inhibitor 10 with a 10-fold increase in activity (IC$_{50}$ of 28 μM). Docking studies suggest that the Abz spacer reproduces the hydrophobic interactions of the native discrete dipeptide β-strand, while reducing the entropy cost of the extended binding conformation of the unbound inhibitor.

A screen of hydrophobic groups appended to the C-terminus (11-17) demonstrated similar activity to C-terminal benzyl derivative 10, which along with reported X-ray structures, suggest the hydrophobic pocket is extensive, see compounds 11, 13-14 in FIG. 3. As expected these hydrophilic peptidic inhibitors showed no cellular activity.

Previous alanine scanning had demonstrated a strict requirement for conservation of both arginines in the N-terminal GRPR amino sequence. The presence of polar N-terminal GRPR residues would also likely hinder cell penetration and useful in vivo activity. The dependence of N-terminal hydrophilic contacts was reexamined using an alanine scan shown in FIG. 3, see compounds 18-20. The results indicate only one arginine residue was necessary to maintain activity, as 18 and 19 possess similar potency to 10.

Figure 4:
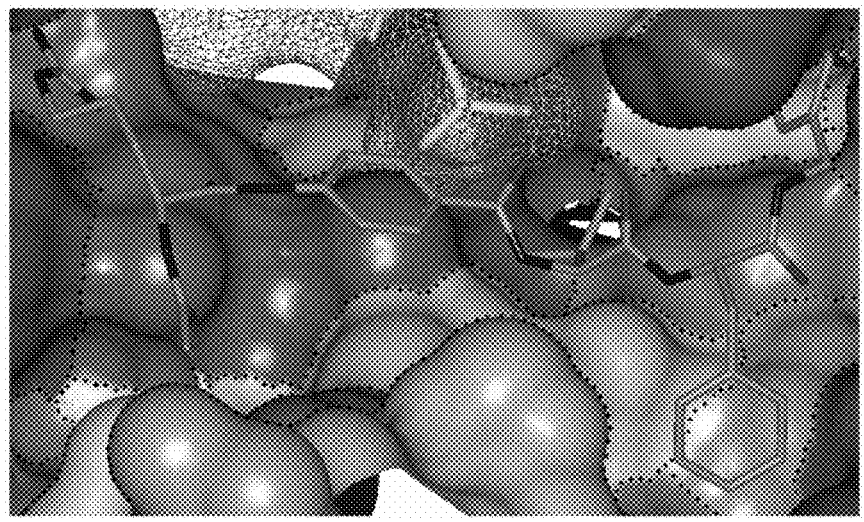
FIG. 4 is an illustration of the crystalline structure of the enzyme-bound compound number 24, the solvent-accessible surface area of activated Akt, and ATP analogue. The Akt surface is shown in a gradient scale with a dashed line delineating the boundaries of the hydrophobic/hydrophilic regions.

The N-terminal -GRP- tripeptide sequence was truncated from the inhibitors. This produced a set of inhibitors with only 3 amino acids and with the optimal hydrophobic substituents coupled to the C-terminus of AcR-Abz-V-F-OH, see compounds 21-25 in FIG. 3. These truncated inhibitors are significantly more hydrophobic than peptidomimetics 1-20, but retain almost identical inhibition potency. Further truncation of the N-terminal acylated amine, shown in compound 26, resulted in an almost two-fold loss of activity when compared to compound 24, highlighting the importance of hydrophobic interactions and the interaction of the carbonyl or amide proton with an adjacent residue, illustrated in FIG. 4.

Figure 5:
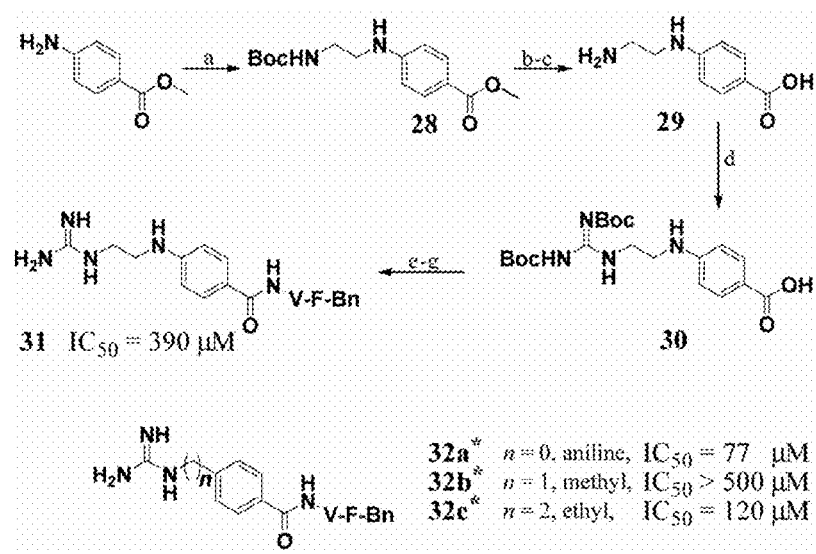
FIG. 5 is a diagram of the synthesis of compounds 28 through 32c. The reaction conditions were (a) 3-phenyl-propionaldehyde, AcOH, NaCNBH3, CH3OH, Mol. Sieves (b) LiOH, THF/H2O (c) TFA (d) BisBocPCH, Et3N, CH3OH (e) HBTU, DIPEA, DMF (f) TFA, 5% thioanisole, 1% TIPS, 1% H2O (g) BnNH2, HATU, DIPEA, DMF. (*Synthesized from commercially available amino benzoic acids following the sequence d-g)

Modifications to the N-terminal hydrophilic residues concentrated on increasing the rigidity and hydrophobicity of the inhibitors; decreasing the length and rotational freedom of the essential guanidinium functionality to project it directly into an acidic pocket of Akt. Different length linkers were explored, with 0, 1, 2, and 3 atoms, seen in FIG. 5, separated from the aromatic spacer to afford inhibitors that showed comparable or better affinity than compound 24 containing the entire Arg residue. Inhibitors with 0-2 atom linkers, 32a-c respectively, were synthesized by the guanidinylation of commercially available amino benzoic acids followed by solid phase coupling, cleavage, and C-terminal coupling. Inhibitor 31, possessing a three atom linker, was synthesized through reductive amination of methyl 4-aminobenzoate with hydrocinnamaldehyde, and subsequent saponification and deprotection to afford compound 29. Guanidinylation of compound 29, proceeded by solid phase coupling, cleavage, and C-terminal coupling to give compound 31. Inhibitor 32a provides the best affinity in this series with an IC$_{50}$ of 77 μM, compared to 500 μM and 120 μM for compounds 32b and 32c, respectively. This suggests that a one atom linker is sufficient to reach the hydrophilic pocket.

Figure 6:
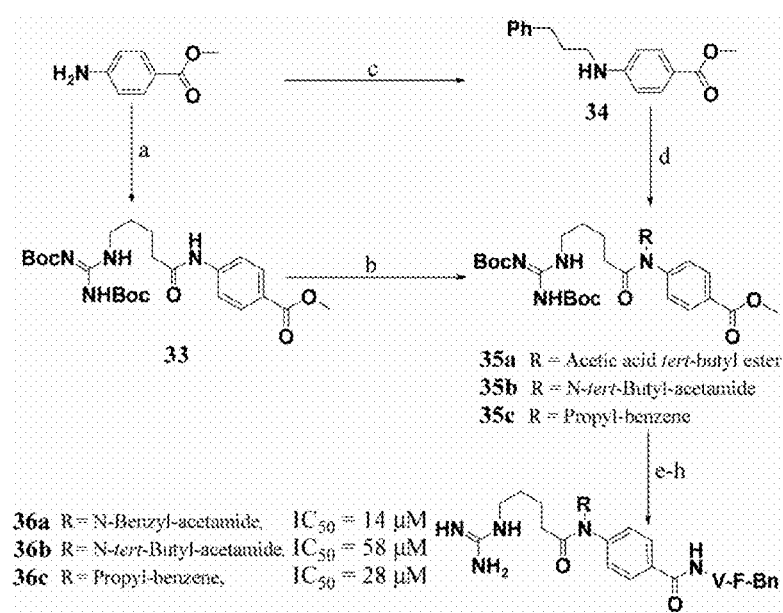
FIG. 6 is a diagram of the synthesis of compounds 28 through 32c. The reaction conditions were (a) compound 27, DIC, $CH_2Cl_2$, cat. DMAP (b) Br-R, Base, DMF (c) 3-phenyl-propionaldehyde, AcOH, $NaCNBH_3$, $CH_3OH$, Mol. Sieves (d) 27, $Ph_3PCl_2$, $CHCl_3$ (e) LiOH, $THF/H_2O$ (f) HBTU, DIPEA, DMF (g) TFA, 5% thioanisole, 1% TIPS, 1% (h) BnNH2, HATU, DIPEA, DMF.

Additional N-terminal modifications focused on scaffolds with a functionalizable handle to access a hydrophobic pocket previously occupied by one of the Thr residues of the GSK3β peptide. Compounds 36a-c were synthesized, shown in FIG. 6, to probe both interactions. Two derivatives were synthesized by coupling 27 and methyl 4-aminobenzoate to afford 33 which was then alkylated with the corresponding bromide to provide 35a-b. Reductive amination of methyl 4-aminobenzoate with 3-phenyl-propionaldehyde followed by coupling with 27 via an in situ acid chloride formation, afforded 35c. Saponification of 35a-c followed by solid phase coupling, cleavage, and C-terminal coupling afforded inhibitors 36a-c.

Figure 7:
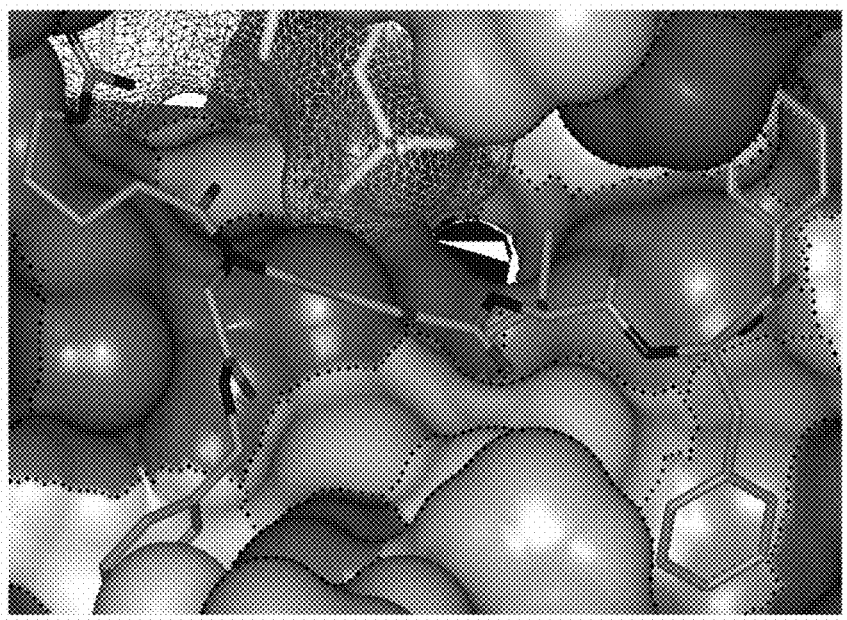
FIG. 7 is an illustration of the crystalline structure of the enzyme-bound compound number 36a, the solvent-accessible surface area of activated Akt, and ATP analogue. The Akt surface is shown in a gradient scale with a dashed line delineating the boundaries of the hydrophobic/hydrophilic regions.

A significant increase in activity was observed with the incorporation of amide functionality and a large hydrophobic group to benzyl derivative 36a, with an IC$_{50}$ of 14 μM. This is significantly higher than the unacylated analog 26. Docking studies of compound 36a suggest that the benzyl substituent projects into a large pocket within the active site of Akt, previously occupied by residues of the GSK3 peptide (FIG. 7). The t-butyl derivative, compound 36b, was slightly less potent with an IC$_{50}$ of 58 μM. Inhibitor 36c was synthesized with similar hydrophobic character as 36a, but lacking the hydrogen bonding potential. Its affinity is comparable to inhibitors 36a, pictured in FIGS. 8, and 36*b*, suggesting that hydrophobic contacts in the Thr pocket are integral to promoting increased affinity.

Figure 8:
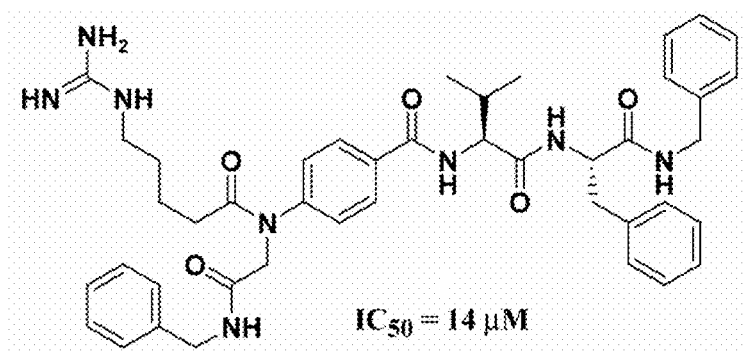
FIG. 8 is a diagram of the chemical structure of compound number 36a, with the structure of valine and phenylalanine drawn out.

In compound 36a, the dipeptide sequence adjacent to the phosphorylated serine/threonine residue was replaced by a 4-aminobenzoic acid (Abz) spacer, seen in FIG. 8. The contacts within this region are mainly hydrophobic, so hydrophobic substituent substitutions were explored from the central phenyl spacer, seen in FIG. 9. A phenyl substituent was incorporated at R2 producing compound 40, with a slight increase in activity compared to previously reported inhibitor 2. Docking studies suggested that the phenyl substituent is able to access the Thr pocket previously exploited in the design of inhibitor 36a. Truncation of the N-terminus of the inhibitors (compounds 42-44) resulted in a modest decrease in affinity, but a desirable decrease in molecular weight and peptidic character of the inhibitors. The study of the central portion of the inhibitor solidified the importance of the projection of substituents into the Thr binding pocket.

Flexible ligand docking (GOLD) of lead peptidomimetics identified several potential replacements for the Val-Phe-Bn C-terminal sequence, which remove two of the three remaining amino acids. A simple cyclic constraints such as quinazolines 50a-b project appended hydrophobic groups into adjacent hydrophobic pockets while maintaining the N-terminal and central inhibitor/Akt interactions, shown in FIG. 10. Inhibitor 50a has similar affinity ($IC_{50}$=112 µM) to the corresponding inhibitor 44 containing the Val-Phe dipeptide, but contains two fewer stereocenters.

Figure 11:
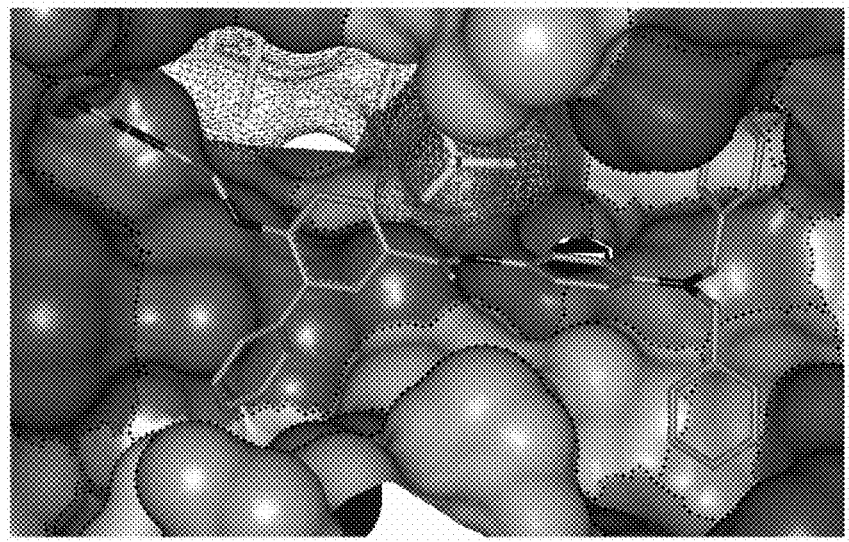
FIG. 11 is an illustration of the crystalline structure of the enzyme-bound compound number 56ba, the solvent-accessible surface area of activated Akt, and ATP analogue. The Akt surface is shown in a gradient scale with a dashed line delineating the boundaries of the hydrophobic/hydrophilic regions.
Figure 12:
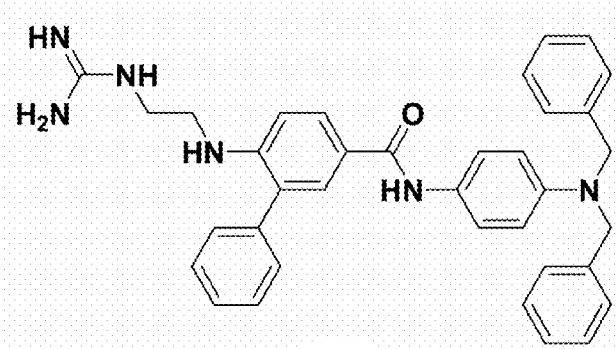
FIG. 12 is a diagram of the chemical structure of compound number 56ba.

Inhibitor 56ba was designed using GOLD to incorporate important binding elements from the previous studies, as seen in FIGS. 11 and 12. The guanidine group is directly projected into the Arg pocket via an ethylenediamine scaffold that extends the correct distance between the aromatic spacer and the arginine binding pocket of Akt. The Thr pocket can be accessed by direct projection of substituents from Abz, shown here as a simple phenyl substituent. Finally, the 4-aminoaniline provides a C-terminal rigid scaffold to project various hydrophobic substituents into the pockets of Akt, with 56ba possessing two benzyl substituents, seen in FIG. 13. This small molecule substrate-mimetic of Akt has an $IC_{50}$ of 84 µM, which is comparable or better than our previous peptidomimetic inhibitors, however is significantly more rigid and impervious to proteases.

Figure 13:
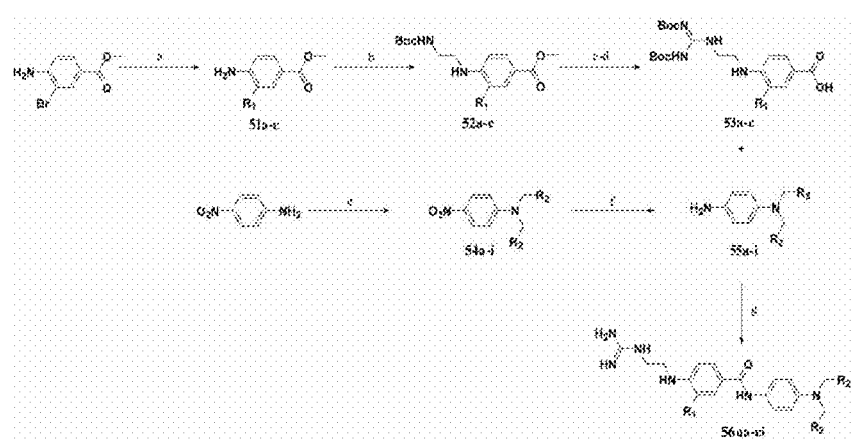
FIG. 13 is a diagram of the synthesis of compounds 51 through 56ci The reaction conditions were (a) $R_1B(OH)_2$, $PdCl_2$(dppf), $K_2CO_3$, DMF, 100° C., 71-82% (13a=methyl 4-aminobenzoate) (b) (i) N-Boc-2-aminoacetaldehyde, AcOH, MeOH, 4 Å mol. sieves (ii) $NaCNBH_3$, 68-100%, (c) (i) LiOH, THF, $H_2O$ (ii) TFA, 70-100% (d) BisBocPCH, $Et_3N$, MeOH, 61-71% (e) RBr, $K_2CO_3$, NaI, DMF, 61-100% (f) $SnCl_2$.2H2O, EtOAc, reflux, 19-92% (g) (i) DIC, cat DMAP, DCM (i) TFA, 26-76%

This non-peptidic scaffold was then explored, using different binding groups, beginning with the C-terminal hydrophobic interactions in series 56aa-56bi, seen in FIGS. 13 and 14. The two pockets are extensive and able to accommodate large hydrophobic substituents (56bd, 56bf, 56bh). Inhibitor 56bi, with a 4-cyanobenzyl functional group, is the most potent inhibitor in this series, having an $IC_{50}$ of 19 µM. Substituents were added directly off Abz to explore the role of contacts within the Thr pocket, producing inhibitors 56aa and 57aa-fa, depicted in FIGS. 14 and 15. Inhibitor 56aa, which lacks the phenyl substituent and the ability to make contacts within this region, is slightly less potent than the biphenyl derivative, suggesting optimization at this position could lead to increased potency. The addition of H-bond donors and acceptors here did not lead to increased affinity (57aa and 57ba), however, larger hydrophobic groups, such as 2-naphthyl, led to a two-fold increase in affinity with inhibitor 57fa having an $IC_{50}$ of 44 µM.

Figure 16:
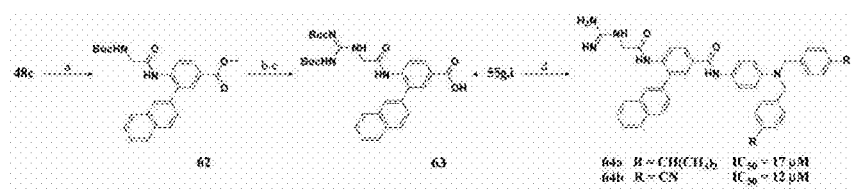
FIG. 16 is a diagram of the synthesis of compounds 62 through 64b. The reaction conditions were (a) Boc-Gly-OH, DIC, cat. DMAP, DCM, 45% (b) (i) LiOH, THF, $H_2O$ (ii) TFA, 90% (c) BisBocPCH, $Et_3N$, MeOH, 54% (d) (i) DIC, cat DMAP, DCM (i) TFA, 57%.

The previous series of non-peptidic substrate-mimetic inhibitors provided valuable information concerning the nature of the three binding pockets within the active site of Akt. To further optimize our inhibitors, the best substituents at the two positions were combined in an effort to increase potency (56cg and 56ci). Inhibitor 56ci, which incorporates the best C-terminal functionality, 4-cyanobenzyl, and the best central element, 2-naphthyl, is the most potent non-peptidic inhibitor of this scaffold series with an $IC_{50}$ of 17 µM, a slight improvement from phenyl derivative 56bi. To increase the stability and rigidity of 56cg and 56ci, the amide analogs 64a-b were synthesized, which also led to a further increase in potency ($IC_{50}$'s=17 µM and 12 µM, respectively), seen in FIG. 16. The initial non-peptidic substrate-mimetic design was successful and optimization of the scaffold provided inhibitors 64a-b that are comparable to inhibitor 36a.

Figure 17:
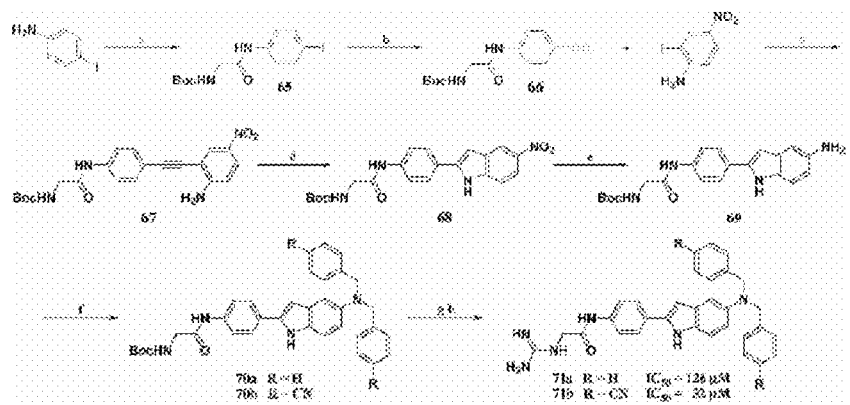
Figure 18:
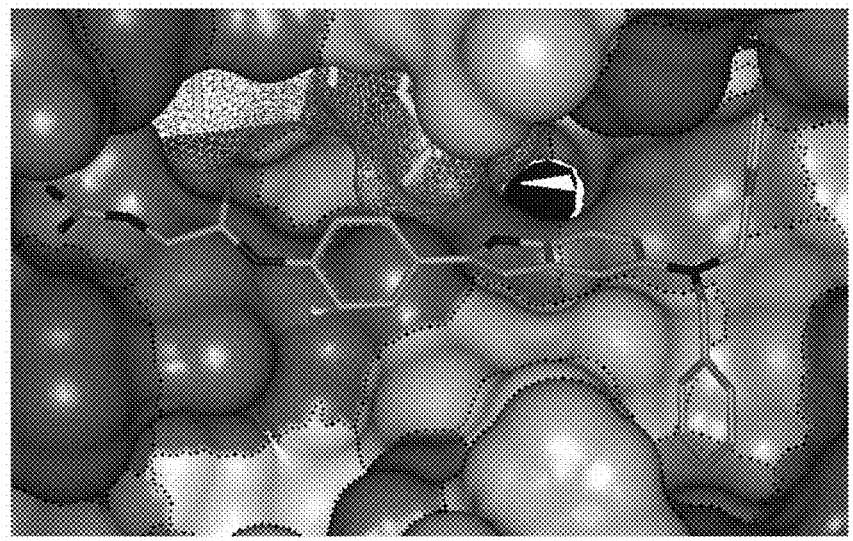
Figure 19:
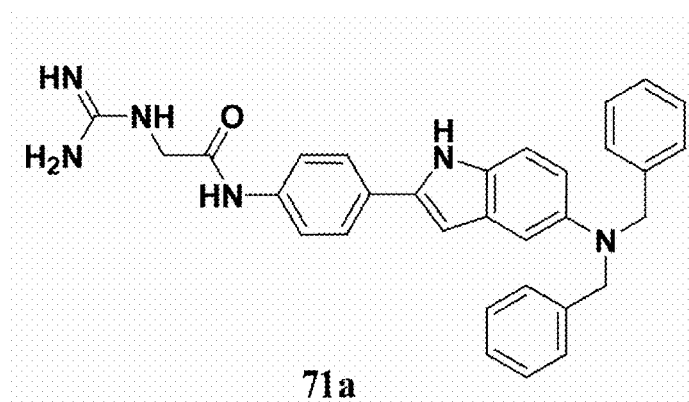
FIG. 19 is a diagram of the synthesis of compounds 65 through 71b. The reaction conditions were (a) Boc-Gly-OH, DIC, cat. DMAP, DCM, 100% (b) (i) TMS-acetylene, CuI, $Pd(PPh_3)_2Cl_1$, $Et_3N$ (ii) $K_2CO_3$, MeOH, 74% (c) CuI, $Pd(PPh_3)_2Cl_2$, 2:1 Et3N:THF, 82% (d) $CuOAc_2$, DMF, 120° C., 3 days, 66% (e) $H_2$ (1 atm), Pd/C, MeOH, 92% (f) RBr, K$_2$CO$_3$, DMF, 100%, 78% (g) (i) 1:1 TFA/DCM (ii) Bis-BocPCH, Et$_3$N, MeOH, 71%, 62% (h) 1:1 TFA/DCM, 32%, 20%.

Optimization focused on increasing rigidity by adding a ring constraint through an indole-aryl scaffold 71a-b, see FIGS. 17. The indole derivative 71a is comparable to 56aa as both lack access to the Thr pocket and possesses C-terminal benzyl substituents, seen in FIGS. 18 and 19. The inclusion of an indole rinscaffold provided a slight decrease in affinity in 71a. Consistent with the previous scaffold, the addition of the C-terminal 4-cyanobenzyl substituent in 71b provided a four-fold increase in affinity from 126 µM to 32 µM.

Synthesis

Peptidomimetics 37-44 were synthesized via solid phase peptide synthesis, using Suzuki couplings employing various boronic acids and aryl bromides. Intermediates display hydrophobic substituents from the aromatic spacer (Abz). The simple quinazoline scaffolds derived from commercially available starting materials. The synthesis of the quinazolines cores 45a-b was accomplished by the cyclization of 4-nitroanthranilic acid by the reaction with sodium isocyanate or cyclization employing a carbon dioxide atmosphere with catalytic DBU (1,8-diazabicyclo[5.4.0]undec-7-ene) from 4- and 5-nitro precursors respectively FIG. 10. Alkylation was followed by reduction of the nitro group followed by coupling with 4-nitrobenzoyl chloride via anilide formation to provide 48a-b. Reduction to the aniline, coupling with AcArg(Pmc)-OH, and deprotection of the guanidine protecting group afforded 50a-b.

A convergent synthesis using methyl-4-amino-2-bromobenzoate or methyl-4-aminobenzoate and 4-nitroaniline created non-peptidic inhibitors 56aa-ci, as seen in FIG. 13. Suzuki coupling of the bromoaniline with the corresponding boronic acid, employing $PdCl_2(dppf)$ as a catalyst, created compounds 51a followed by reductive amination utilizing N-Boc-aminoacetaldehyde produced compounds 52a-c. A series of deprotections followed by guanidinylation of the resulting amine afforded the N-terminal portions of the inhibitor 53a-c. The C-terminal hydrophobic portion of the molecule was synthesized via alkylation of 4-nitroaniline with the corresponding bromide and subsequent reduction of the nitro group utilizing tin (II) chloride, producing compounds 55a-i. Coupling of compounds 53a-c and 55a-i followed by Boc deprotection under acidic conditions produced inhibitors 56aa-ci. Inhibitors 64a-b were derived from a similar synthesis, but in place of the reductive amination step, 48c was reacted with Boc-Gly-OH to provide the amide intermediate compound 62 which was manipulated in a similar manner to provide inhibitors 64a-b, seen in FIG. 16.

Figure 15:
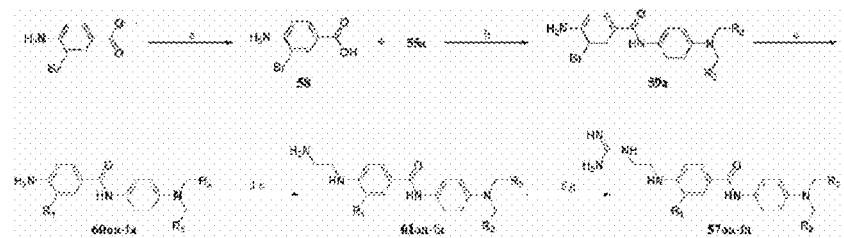
FIG. 15 is a diagram of the synthesis of compounds 58 through 61fa and inhibitors 57aa through 57fa. The reaction conditions were (a) LiOH, THF, $H_2O$, 100% (b) DIC, cat DMAP, DCM (c) $R_1B(OH)_2$, $PdCl_2$(dppf), $K_2CO_3$, DMF, 100° C., 62-78% (d) (i) N-Boc-2-aminoacetaldehyde, AcOH, MeOH, 4 Å mol. sieves (ii) $NaCNBH_3$ (e) TFA, 41-69%, (f) BisBocPCH, $Et_3N$, MeOH, 51-88% (g) TFA, 40-99%.

The synthesis of inhibitors 57aa-fa was designed to employ a late stage Suzuki coupling to provide faster access to a number of derivatives at the $R_1$ position, while keeping $R_2$ as a benzyl substituent, see FIG. 15. Commercially available methyl-4-amino-3-bromobenzoate was saponified under basic conditions followed by amide bond formation with compound 55a to provide compound 59a. This intermediate was then reacted with different boronic acid derivatives $PdCl_2(dppf)$ as a catalyst to provide 60aa-fa. A series of functional group transformations provided inhibitors 57aa-fa.

The indole scaffold was readily derived from commercially available 4-iodoaniline and Boc-Gly-OH, which were reacted to form iodo-amide compound 65, seen in FIG. 17.

Figures 9, 10:
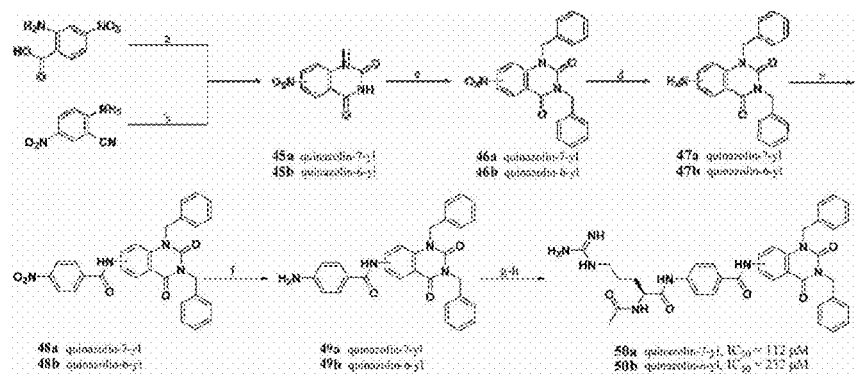
FIG. 9 is a table of investigations into the hydrophobic interactions between the GSK-3 residues central hydrophobic contacts and Akt. The values reported are an average of three independent binding curves using an IMAP™ Akt Assay Kit (Molecular Devices). Reactions were conducted in wells with 20.0 µL of 10 mM Tris-HCl (pH 7.2), 10 mM $MgCl_2$, 0.1% BSA, 0.05% $NaN_3$, 1 mM DTT, 100 nM 5FAM-GRPRTSSFAEG-COOH, 5 µM ATP, Akt1, and inhibitor. Reaction mixtures were incubated for 1 h at room temperature and then quenched with 60 µL of the IMAP-binding solution. The reactions were equilibrated for 1 h at room temperature then data points were collected and analyzed.
FIG. 10 is a diagram of the synthesis of compounds 45 through 50c. The reaction conditions were (a) i. NaNCO, ii. NaOH, iii. HCl, 53% (b) $CO_2$ 1atm, DBU, THF, 82% (c) $K_2CO_3$, BnBr, DMF, 81%, 91% (d) Pd/C, $H_2$ 35 psi, $CH_3OH$, 88%, 81% (e) i. LDA, THF, ii. 4-nitro benzoyl chloride −78° C.-50 ° C., 76%, 81% (f) Pd/C, $H_2$ 35 psi, 1:1 $CH_3OH$: $CH_2Cl_2$, 80%, 86% (g) AcArg(Pmc)-OH, DIC, $CH_2Cl_2$, cat. DMAP (h) TFA, 5% thioanilsole, 1% TIPS, 1% $H_2O$, 4%, 5%

Sonagashira cross-coupling of compound 65 and ethynyl-trimethyl-silane (TMS-acetylene) followed by removal of the silyl protecting group afforded terminal alkyne compound 66. A consecutive Sonagashira cross-coupling with 2-iodo-4-nitroaniline followed by cycloisomerization employing catalytic copper (II) acetate[41] afforded indole scaffold compound 68. Reduction of the nitro to the amine followed by alkylation with the cooresponding bromide provided compound 70a-b. A series of functional group transformations, similar to the reactions depicted in FIGS. 10 and 13, provided inhibitors 71a-b.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments herein, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of inhibiting AKT in cells comprising the steps of:
   introducing an effective amount of a substrate mimetic inhibitor of AKT into the cell, wherein the substrate mimetic inhibitor has a formula G-R-P-R-A-A-V-F, or G-R-P-R-linker-V-F-end cap;
   wherein G is glycine, R is arginine, P is proline, T is threonine, W is tryptophan, F is phenylalanine, H is histidine, V is valine, A is alanine, C is cysteine, and N is asparagine;
   wherein the linker is:

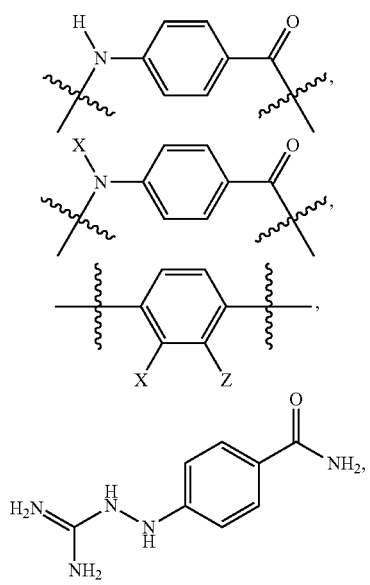

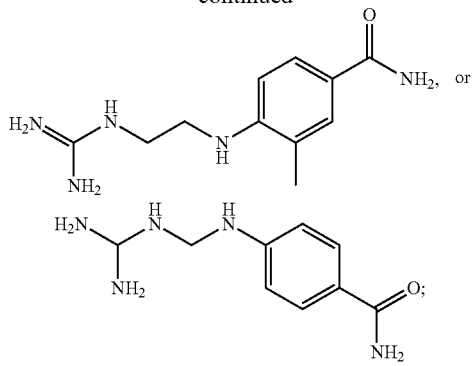

where X is N-benzyl acetamide;
where Y is hydrogen, methyl, or phenyl;
where Z is hydrogen, phenyl, or napthyl; and
wherein the end cap is:

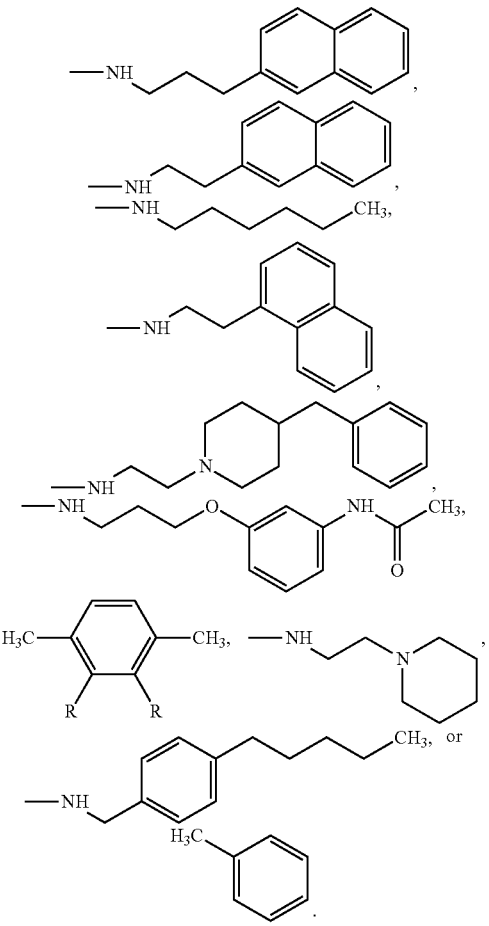

2. The method of claim 1, wherein the linker is p-amino benzoic acid or 4-aminobenzoic acid.

3. An inhibitor of Akt comprising a substrate mimetic compound, wherein the inhibitor has a formula G-R-P-R-A-A-V-F, or G-R-P-R-linker-V-F-end cap;
   wherein G is glycine, R is arginine, P is proline, T is threonine, W is tryptophan, F is phenylalanine, H is histidine, V is valine, A is alanine, C is cysteine, and N is asparagine;

wherein the linker is:

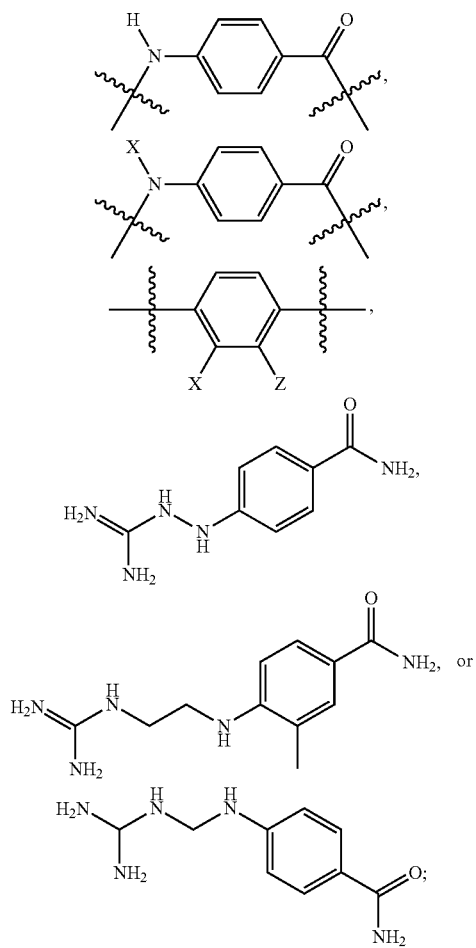

where X is N-benzyl acetamide;
where Y is hydrogen, methyl, or phenyl;
where Z is hydrogen, phenyl, or napthyl; and
wherein the end cap is:

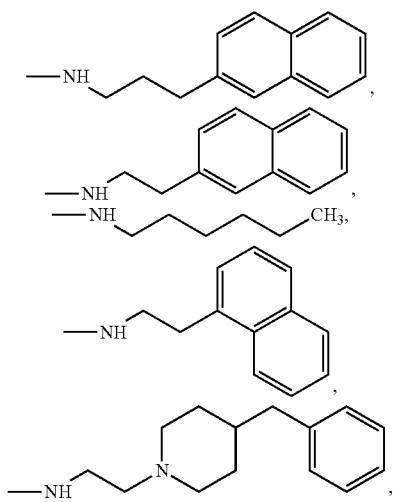

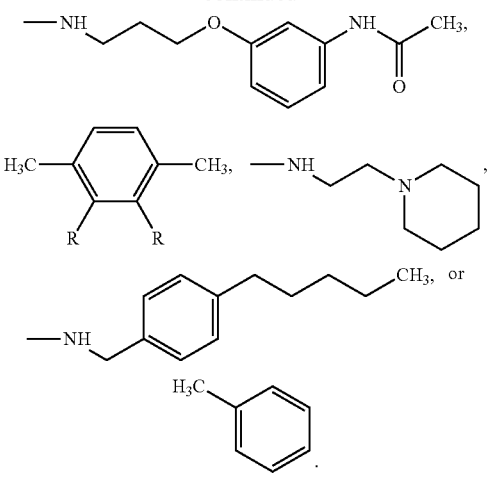

4. A method of inhibiting AKT in cells comprising the steps of:
introducing an effective amount of a substrate mimetic inhibitor of AKT into the cell, wherein the substrate mimetic inhibitor has a formula G-R-P-R-linker-V-F-end cap;
wherein G is glycine, R is arginine, P is proline, T is threonine, W is tryptophan, F is phenylalanine, H is histidine, V is valine, A is alanine, C is cysteine, and N is asparagine;
wherein the linker is:

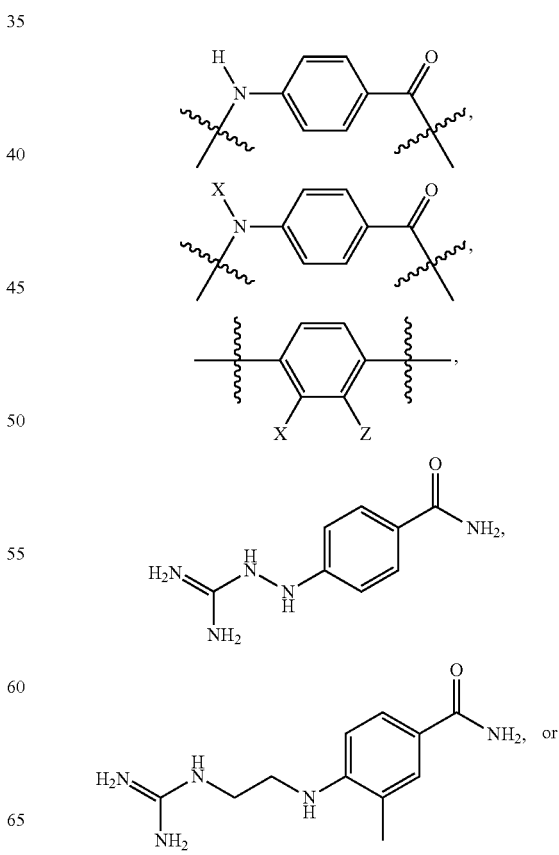

-continued

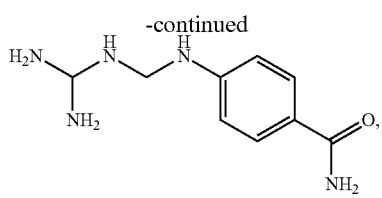

or AA;
where X is N-benzyl acetamide;
where Y is hydrogen, methyl, or phenyl;
where Z is hydrogen, phenyl, or napthyl; and
wherein the end cap is:

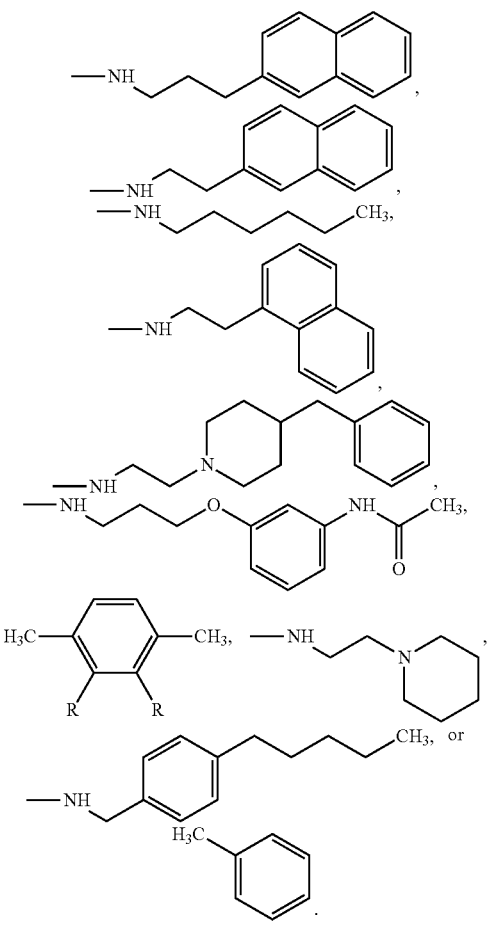

5. The method of claim 4, wherein Y is hydrogen and Z is hydrogen, phenyl, or 1-napthyl.

6. The method of claim 4, wherein Y is methyl and Z is hydrogen.

7. The method of claim 4, wherein Y is phenyl and Z is hydrogen.

8. The method of claim 4, wherein the linker is p-amino benzoic acid or 4-aminobenzoic acid.

9. An inhibitor of Akt comprising a substrate mimetic compound, wherein the inhibitor has a formula G-R-P-R-linker-V-F-end cap;
wherein G is glycine, R is arginine, P is proline, T is threonine, W is tryptophan, F is phenylalanine, H is histidine, V is valine, A is alanine, C is cysteine, and N is asparagine;

wherein the linker is:

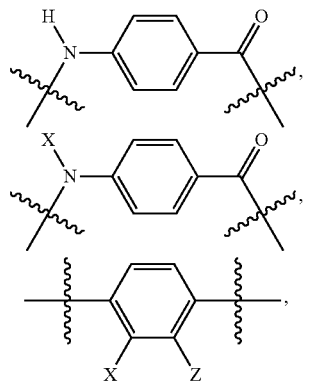

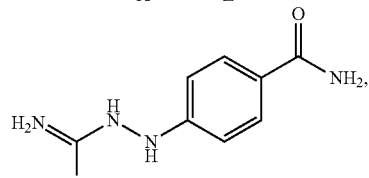

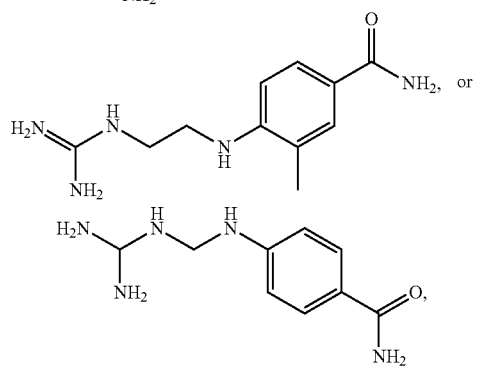

or AA;
where X is N-benzyl acetamide;
where Y is hydrogen, methyl, or phenyl;
where Z is hydrogen, phenyl, or napthyl; and
wherein the end cap is:

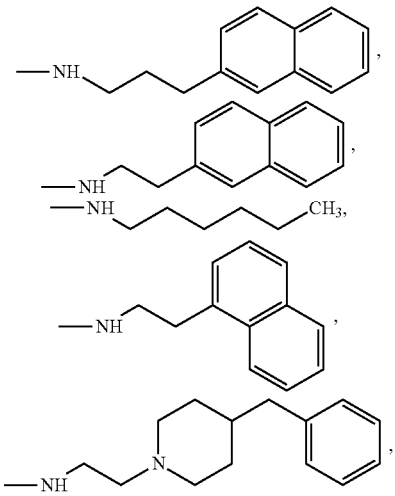

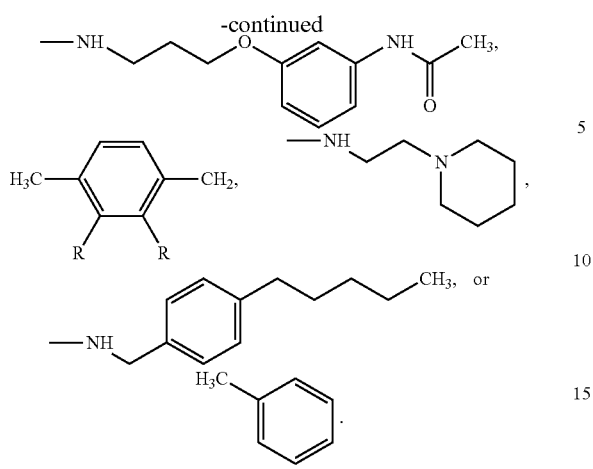
10. The inhibitor of claim 9, wherein Y is hydrogen and Z is hydrogen, phenyl, or 1-napthyl.
11. The inhibitor of claim 9, wherein Y is methyl and Z is hydrogen.
12. The inhibitor of claim 9, wherein Y is phenyl and Z is hydrogen.
13. The inhibitor of claim 9, wherein the linker is p-amino benzoic acid or 4-aminobenzoic acid.
* * * * *